US012582498B2

(12) United States Patent
Padoy et al.

(10) Patent No.: US 12,582,498 B2
(45) Date of Patent: Mar. 24, 2026

(54) PROCESSING OF VIDEO STREAMS RELATED TO SURGICAL OPERATIONS

(71) Applicants: FONDATION DE COOPERATION SCIENTIFIQUE, Strasbourg (FR); Université de Strasbourg, Strasbourg (FR); CENTRE NATIONAL DE LA RECHERCHE SCIENTIFIQUE—CNRS –, Paris (FR); UNIVERSITÀ CATTOLICA DEL SACRO CUORE, Milan (IT); INSTITUT DE RECHERCHE CONTRE LES CANCERS DE L'APPAREIL DIGESTIF, Strasbourg (FR)

(72) Inventors: Nicolas Padoy, Strasbourg (FR); Pietro Mascagni, Rome (IT); Bernard Dallemagne, Beaufays (BE)

(73) Assignees: FONDATION DE COOPERATION SCIENTIFIQUE, Strasbourg (FR); UNIVERSITÉ DE STRASBOURG, Strasbourg (FR); CENTRE NATIONAL DE LA RECHERCHE SCIENTIFIQUE—CNRS, Paris (FR); UNIVERSITÀ CATTOLICA DEL SACRO CUORE, Milan (IT); INSTITUT DE RECHERCHE CONTRE LES CANCERS DE L'APPAREIL DIGESTIF, Strasbourg (FR)

( * ) Notice: Subject to any disclaimer, the term of this patent is extended or adjusted under 35 U.S.C. 154(b) by 438 days.

(21) Appl. No.: 18/009,830

(22) PCT Filed: Jun. 11, 2021

(86) PCT No.: PCT/FR2021/051053
§ 371 (c)(1),
(2) Date: Dec. 12, 2022

(87) PCT Pub. No.: WO2021/250362
PCT Pub. Date: Dec. 16, 2021

(65) Prior Publication Data
US 2023/0240788 A1 Aug. 3, 2023

(30) Foreign Application Priority Data
Jun. 12, 2020 (FR) ...................................... 2006178

(51) Int. Cl.
*G06V 10/70* (2022.01)
*A61B 90/00* (2016.01)
(Continued)

(52) U.S. Cl.
CPC ........... *A61B 90/361* (2016.02); *A61B 90/37* (2016.02); *G06V 10/70* (2022.01); *G16H 30/20* (2018.01); *G16H 50/30* (2018.01)

(58) Field of Classification Search
CPC ...... A61B 90/361; A61B 90/37; G06V 10/70; G06V 20/41; G06V 20/44; G16H 30/20; G16H 50/30
See application file for complete search history.

(56) References Cited

U.S. PATENT DOCUMENTS 8,953,674 B2 * 2/2015 Henson .................. H04N 7/188
375/240.09
9,049,348 B1 * 6/2015 Foster .................... H04N 7/183
(Continued)

FOREIGN PATENT DOCUMENTS

EP 3593704 A1 1/2020
FR 3012640 A1 10/2013
(Continued)

OTHER PUBLICATIONS

International Search report dated Sep. 28, 2021, in International Application No. PCT/FR2021/051053 (7 pages).
(Continued)

*Primary Examiner* — Stephen S Hong
*Assistant Examiner* — Darrin Hope
(74) *Attorney, Agent, or Firm* — Maier & Maier, PLLC

(57) ABSTRACT

A device for processing a video stream related to a specific operative procedure. The device includes: a video stream reception interface, a processor, and a memory storing instructions, such that when the instructions are executed by the processor, they configure the device for: receiving, via the video stream reception interface, the video stream having a sequence of images including an image to be processed which represents at least a portion of an anatomical element, the image to be processed being formed by processing elements; determining, by a processing function, whether or not a criterion is satisfied in the image to be processed; determining a state of progress associated with the image to be processed based on whether or not the criterion is satisfied, the state of progress being representative of a state of progress of an operative step of the specific operative procedure.

20 Claims, 2 Drawing Sheets

(51) Int. Cl.
*G16H 30/20* (2018.01)
*G16H 50/30* (2018.01)

(56) References Cited

U.S. PATENT DOCUMENTS

| | | | | |
|---|---|---|---|---|
| 10,262,192 | B2 * | 4/2019 | Silva | G06V 40/165 |
| 10,574,892 | B2 * | 2/2020 | Burgess | H04N 5/272 |
| 10,846,875 | B2 * | 11/2020 | Etcheverry | G06N 20/10 |
| 11,398,038 | B2 * | 7/2022 | Yu | G06T 7/254 |
| 11,475,667 | B2 * | 10/2022 | Yakupov | G06V 20/46 |
| 12,315,609 | B2 * | 5/2025 | Wolf | G16H 50/70 |
| 2013/0223715 | A1 * | 8/2013 | Jerebko | G06T 7/0012 |
| | | | | 382/131 |
| 2013/0227609 | A1 * | 8/2013 | Winter | H04N 21/47205 |
| | | | | 725/37 |
| 2015/0227805 | A1 * | 8/2015 | Stokman | H04N 23/611 |
| | | | | 382/286 |
| 2018/0247128 | A1 | 8/2018 | Alvi et al. | |
| 2018/0366231 | A1 | 12/2018 | Wolf et al. | |
| 2019/0069957 | A1 * | 3/2019 | Barral | A61B 34/20 |
| 2019/0223961 | A1 | 7/2019 | Barral et al. | |
| 2019/0333626 | A1 | 10/2019 | Mansi et al. | |
| 2019/0354753 | A1 * | 11/2019 | Worrall | G06V 40/20 |
| 2019/0362834 | A1 | 11/2019 | Venkataraman et al. | |
| 2019/0378291 | A1 * | 12/2019 | Etcheverry | G16H 30/40 |
| 2020/0170710 | A1 | 6/2020 | Rus et al. | |
| 2020/0268469 | A1 * | 8/2020 | Wolf | A61B 5/7275 |
| 2021/0158939 | A1 * | 5/2021 | Mathur | G16H 30/40 |
| 2021/0174503 | A1 * | 6/2021 | Trautwein | G16H 50/70 |
| 2021/0289171 | A1 * | 9/2021 | Sarkar | H04N 7/183 |
| 2022/0202508 | A1 * | 6/2022 | Hiranandani | G06N 20/00 |

FOREIGN PATENT DOCUMENTS

| | | | | |
|---|---|---|---|---|
| WO | WO-2014136623 A1 * | 9/2014 | | G06V 20/00 |
| WO | 2015066565 A1 | 5/2015 | | |
| WO | 2017220788 A1 | 12/2017 | | |
| WO | 2018012080 A1 | 1/2018 | | |
| WO | 2018163644 A1 | 9/2018 | | |
| WO | 2019040705 A1 | 2/2019 | | |
| WO | 2020023740 A1 | 1/2020 | | |
| WO | WO-2022221342 A1 * | 10/2022 | | G06N 3/09 |

OTHER PUBLICATIONS

Pietro Mascagni et al., "Formalizing Video Documentation of the Critical View of Safety in laparoscopic cholecystectomy: a step towards artificial intelligence assistance to improve surgical safety", Surgical Endoscopy, 2019, (8 pages).
Chinedu Innocent Nwoye et al. "Weakly Supervised Convolutional LSTM Approach for Tool Tracking in Laparoscopic Videos", International Journal of Computer Assisted Radiology and Surgery, 2019 (pp. 1-14).
Andru P. Twinanda et al., "EndoNet: A Deep Architecture for Recognition Tasks on Laparoscopic Videos", IEEE Transactions on Medical Imaging, 2016, (11 pages).
Siddharth Kannan et al., "Future-State Predicting LSTM for Early Surgery Type Recognition", IEEE Transactions on Medical Imaging, 2020, (10 pages).
Andru P. Twinanda et al., "RSDNet: Learning to Predict Remaining Surgery Duration from Laparoscopic Videos Without Manual Annotations", IEEE Transactions on Medical Imaging, 2019, (10 pages).
Florent Lalys et al., "Automatic Phases Recognition in Pituitary Surgeries by Microscope Images Classification", IPCAI, 2010, (pp. 34-44).
Sakabe et al., "Proposal of Surgery Video Archiving System for Supporting Risk Detection Using Infrequent Motion Recognition", Information Processing Society of Japan, Jul. 2011, vol. 4, No. 3, pp. 122-131, with English abstract.
Marutani et al., "Development of Surgical Skills Training System to Teach Expert Physician's Skill Appropriate for Surgical Process", IEICE, May 2016, pp. 53-58, with English abstract.

* cited by examiner

PROCESSING OF VIDEO STREAMS RELATED TO SURGICAL OPERATIONS

CROSS-REFERENCE TO RELATED APPLICATIONS

This application claims priority benefit under 35 U.S.C. § 119(d) from French Patent Application No. FR2006178, filed Jun. 12, 2020, the disclosure of which is incorporated by reference herein in its entirety.

FIELD

The present subject disclosure relates to the field of analysis and computer processing of data related to video streams, and in particular to video streams related to surgical operations It has applications in particular in video stream processing devices which make it possible to improve safety during surgical operations. For example, a surgeon assistance device.

BACKGROUND

In particular, there are protocols or guidelines to reduce complications related to surgery. However, these protocols or guidelines are not necessarily applied properly.

For example, in the case of removal of the gallbladder, a protocol has been developed for identifying organs and their positioning during surgery, called the "critical view of safety" (CVS).

The CVS relates to three independent criteria related to the positioning of the organs, which must be satisfied before the ablation. In other words, the surgeon must perform dissection in order to modify the anatomy of the organs involved, and, based on his or her observations, must determine to what extent the three criteria are satisfied before proceeding to the step posing a high risk for the patient.

Despite substantial results in reducing complications related to this type of surgery, CVS is not often followed or not necessarily properly applied. Moreover, the reliability of the surgeon's observations is not constant. Thus, even when the CVS protocol is applied, errors in judgment may occur.

SUMMARY

The present subject disclosure improves the situation.

A first aspect of the subject disclosure relates to a device for processing a video stream related to a specific operative procedure, said device comprising:
a video stream reception interface;
a processor; and
a memory storing instructions, such that when these instructions are executed by the processor, they configure the device for:
   receiving, via the video stream reception interface, the video stream comprising a sequence of images including an image to be processed which represents at least a portion of an anatomical element, said image to be processed being formed by processing elements;
   determining, by means of a processing function, whether or not at least one criterion is satisfied in the image to be processed, the processing function being composed of a first parameterized function and a second parameterized function:

parameters of the first parameterized function being obtained by a machine learning algorithm on the basis of an image from a reference sequence of images such that the result of the first parameterized function applied to the image allows determining the processing elements of the image which represent the portion of the anatomical element, the reference sequence of images being previously recorded and related to the specific operative procedure, the image from the reference sequence of images representing at least a portion of an anatomical element,
parameters of the second parameterized function being obtained by a machine learning algorithm on the basis of the image from the reference sequence of images combined with a result of the first parameterized function applied to the image from the reference sequence of images such that the result of the second parameterized function applied to the image, combined with a result of the first parameterized function applied to the image, allows determining whether or not the at least one criterion is satisfied;
determining a state of progress associated with the image to be processed, based on whether or not the criterion is satisfied, the state of progress being representative of a state of progress of an operative step of the specific operative procedure.

It is thus possible to automatically assess the state of progress of an operative step, on the basis of an image from the video stream of the specific operative procedure. In other words, analyzing the image makes it possible to determine the point at which the image is located within the operative protocol. This analysis is done by applying a processing function to the image, the result of this processing function indicating whether or not one or more criteria are satisfied. The point at which the image is located within the operative protocol is determined, based on the criteria validation. It is thus no longer necessary to rely on the surgeon's observations to determine the state of progress of a surgical operation. The state of progress can then be used to provide real-time information to the surgeon. For example: the surgeon is properly following the protocol, validation before moving on to the next stage of the protocol, an alert concerning vital and/or sensitive and/or barely visible organs, or informing of an anatomical element with specific anatomical characteristics. The state of progress can also allow modifying the parameters of the video to adapt to the operative step. For example, it is possible to zoom in on an area of interest, to increase the contrast, or to modify the colorimetry. It is also possible to store critical operative steps at a higher definition. It is also possible to modify the operating room schedule according to the state of progress of the operative step.

Specific operative procedure is understood to mean a specific medical procedure, for example a surgical procedure. In other words, specific operative procedure is understood to mean a type of medical procedure or a type of operative procedure.

Video stream is understood to mean a sequence of images encoded according to a video format (for example MPEG2, H.264/AVC, HEVC, VP8, VP9, AV1). The video stream may come from a video camera, in particular a micro-camera which can be introduced into the patient's body.

Processing elements is understood to mean the processing units of the images of the sequence, for example pixels. These processing units are specific to the device, but may match those of the video format, for example macroblocks (MB) or coding tree units (CTU).

Anatomical element is understood to mean an organ of the body. The image that displays this anatomical element represents it.

Several criteria (also called anatomical criteria) may be determined on the first image. Determination of the state of progress may be independent of the order in which these criteria were satisfied during the processing of the previous images.

Reference sequence of images is understood to mean a sequence of images filmed prior to recording the video from which the video stream is received. This is a sequence of images related to the same type of operative procedure as that of the video stream.

Operative step is understood to mean a step in the specific operative procedure. State of progress of the operative step is understood to mean a level of progress or a level of completeness representative of the progress or the completeness of the operative step, for example the percentage of completion of the step.

The processing function is composed of two parameterized functions. For example, the first parameterized function is first applied to the image, and the second parameterized function is then applied to the combination of the result of the first parameterized function and this same image. In other words, the second parameterized function is applied to the result of the first parameterized function $f_1(I)$ and the image I, i.e. to the couple $(f_1(I); I)$.

The first parameterized function may be obtained by a machine learning algorithm trained on an image from a reference sequence of images (and more generally on a collection of images) such that the parameterized function returns the expected result or at least the closest possible result. For example, the parameterized function may be obtained by optimizing the parameters of an artificial neural network by applying a machine learning algorithm to the image (or the collection of images). The machine learning algorithm determines the parameters so that they optimize (for example minimize) the result of a cost function calculated for the values of the processing elements (or simply on the processing elements—for example the pixels of the image) of the image from the reference sequence of images (and generally on a large set of images), said processing element being representative of the portion of the anatomical element. The cost function may be a distance between the result of the first parameterized function applied to a processing element and the expected result, namely the result which represents whether or not the image processing element belongs to the portion of the anatomical element. The first parameterized function makes it possible to perform segmentation of the image to which it is applied, according to the portion of the anatomical element or more generally the various anatomical elements present in the image.

The first parameterized function is thus parameterized to allow determining the image processing elements representative of the portion of the anatomical element. More specifically, the first parameterized function determines the processing elements, identifies them, gives labels or more generally assigns a value to each processing element of the image to be processed, according to whether or not it belongs to the portion of the anatomical element. The first function may determine several different anatomical elements when the criteria to be satisfied require several anatomical elements to be taken into account. By using a machine learning algorithm, the determination of the parameters of the first parameterized function is more precise.

Furthermore, the determination of the group of processing elements is then less sensitive to the anatomical element, i.e. to the variations in the anatomical element from one patient to another. The determination is therefore less subject to errors.

The second parameterized function may be obtained by a machine learning algorithm trained on the image from the reference sequence of images (and more generally on a collection of images) combined with the result from the first parameterized function applied to the image from the reference sequence of images (training can be done effectively with the result from the first parameterized function or directly with the expected solution, namely whether or not the image processing elements belong to the portion of the anatomical element) so that the parameterized function returns the expected result or at least the closest possible result. For instance, the parameterized function may be obtained by optimizing parameters of an artificial neural network by applying a machine learning algorithm to the image (or collection of images) combined with the result from the first parameterized function or the expected solution.

The combination of the image from the reference sequence of images and the result of the first parameterized function applied to the image from the reference sequence of images (or directly with the expected solution, namely whether or not the processing elements of the image belong to the portion of the anatomical element) is here simply called a combination related to the image from the reference sequence of images or alternatively a reference combination.

The machine learning algorithm determines the parameters of the second parameterized function so that they optimize (for example, minimize) the result of a cost function calculated on a reference combination (and more generally on a large set of combinations related to reference images). The cost function may be a distance between the result of the second parameterized function applied to a reference combination and the expected result, namely the result which represents whether or not the criterion or criteria are satisfied for this reference combination.

The combinations of an image and the result of the first parameterized function applied to this image or of the expected solution may be an n-tuple of matrices whose cells represent the processing elements. For example, three of the n matrices are used to code the processing elements (for example pixels) according to an RGB color code. Each other matrix of the n-tuple represents a different anatomical element. The cells of a matrix which represent an anatomical element have values (for example 1 or 0) which depend on whether or not the processing element (corresponding to the cell) belongs to the anatomical element.

The parameters of the first and second parameterized function may be stored in memory.

By using a machine learning algorithm, the determination of whether or not the criterion is satisfied is more accurate.

The two machine learning algorithms used to obtain the first and the second parameterized functions are independent of each other. Thus, it is possible in particular to perform the learning on separate databases and to better control the learning of each of the algorithms, thus making it possible to have a greater learning efficiency while requiring less computing power.

Thus, this disjoint learning of the two parameterized functions, rather than the learning of a single function that would be applied to the images and would allow directly obtaining the result of each criterion, makes it possible to determine more effectively (in particular with less error or with even more precision) whether or not the criterion is satisfied. Indeed, by enriching the image with, for each processing element of the image to be processed, a value depending on whether or not the element belongs to the portion of the anatomical element, there is less risk of anatomical elements being misinterpreted by the second parameterized function and thus of the criteria being improperly evaluated.

The state of progress associated with the image to be processed may be determined according to the verification of several criteria (C1, C2, C3); for example, each validation combination of the criteria (1, 0, 1), (1, 0, 0), etc. returns to a different state of progress.

According to one embodiment, when the instructions are executed by the processor, they configure the device for:

based on the determined state of progress, storing images from the sequence of images that are within a time interval around the image to be processed.

It is thus possible to store part of the video stream corresponding to critical operative steps, or to store this part of the video stream in a less compressed manner, meaning with greater definition and/or retaining more frames of this part of the video stream. The center where the operation took place can then keep the most relevant elements of each operation.

According to one embodiment, the number of images stored is dependent on the criticality of the operative step and/or on the determined state of progress.

It is thus possible to optimize the storage space required for storing the sequence of images.

According to one embodiment, a display means is also provided, and, when the instructions are executed by the processor, they configure the device for:

displaying on the display means, with the image to be processed, information dependent on the state of progress.

The surgeon or any person involved in the operative procedure can thus be made aware of the state of progress of the operative procedure.

According to one embodiment, when the instructions are executed by the processor, they configure the device for:

determining a deviation from an operative protocol, on the basis of the state of progress;

where the information dependent on the state of progress is dependent on the determined deviation.

It is thus possible to display information dependent on the determined deviation (for example, an alert) when the operative step of the specific operative procedure does not comply with an operative protocol (for example, an operative protocol determined at the start of the operative procedure).

The display means may in particular be done on the means used to display the video stream to the surgeon, for example by means of a screen or an immersive viewing device (for example, with virtual reality glasses).

Operative protocol is understood to mean the set of scheduled operating tasks for carrying out the specific operative procedure.

The information dependent on the deviation is displayed on the display means: it may be inserted into the video stream displayed to the surgeon, as indicated above, for example in augmented reality.

The deviation may be a difference from the operative protocol according to one or more specific indicators; for example, based on the state of progress, if the surgeon performs an action which transforms the portion of the anatomical element or a portion of another anatomical element present in the images of the sequence which does not correspond to the transformation expected according to the operative protocol. The deviation may also correspond to a time lag between the time corresponding to the state of progress in the sequence of images and the time corresponding to the same state of progress in the reference sequence of images.

According to one embodiment, the display of information dependent on the state of progress is according to a criticality of the operative step represented by the state of progress.

The information dependent on the state of progress, for example the information related to the deviation, could thus be an alert or simple information depending on whether or not the operative step is critical.

According to one embodiment, the information dependent on the state of progress comprises information indicating that the criterion is not validated.

The surgeon or any person involved in the operation can thus, in real time, determine the actions or tasks to be carried out in order to perform the operative act correctly. The criterion which is not validated is, for example, a criterion which, in view of the operative protocol, should have been validated at this stage in the progress.

According to one embodiment, the information dependent on the first state of progress comprises information validating a sub-step, a surgical maneuver and/or surgical action of an operative step, or information authorizing the start of a next operative step.

It is thus a matter of informing the surgeon that the operative step is advancing correctly or indicating the next operative step to the surgeon, or validating the current operative step in order to allow advancing to the next operative step.

According to one embodiment, when the instructions are executed by the processor, they configure the device for:

determining a deviation between at least one value of a characteristic of a group of processing elements of the image which represent the portion of the anatomical element and a reference value, the reference value being an average of the value of the characteristic of groups of processing elements which represent the portion of the anatomical element and are related to the same state of progress as the state of progress;

determining a level of risk associated with this deviation;

wherein the information dependent on the state of progress includes the level of risk.

It is thus possible to alert the surgeon when an anatomical element is abnormal.

The characteristic of the group of elements may be, for example, the size of the group of processing elements, the shape of the group of processing elements, the arrangement of this group of processing elements, or the color of the group of processing elements.

The level of risk may be defined by ranges of values which include the average value. Any value of the characteristic outside the range of values will be considered as presenting a level of risk.

Several thresholds (or ranges of values) may be defined for each monitored characteristic; thus, several levels of risk can be determined.

The reference value may be obtained by averaging the values of the characteristic of groups of elements that are obtained from a plurality of reference sequences of images, the groups of elements being those at the same state of progress as the first state of progress.

In addition, the determination of the deviation between the value of the characteristic of the group of processing elements and a reference value is made more efficient because it uses the group of processing elements determined beforehand, thus not requiring any new determination.

According to one embodiment, the information dependent on the state of progress includes:

a zone in which a surgical action is to be performed; and/or a zone in which there is no surgical action; and/or a zone in which there is an anatomical element requiring special attention; and/or a zone corresponding to processing elements that are considered for the first state of progress.

It is thus possible to display, on the display means displaying the video stream to the surgeon, a zone which changes with the progress. This zone may be displayed by highlighting or by delimiting the outline of this zone. Thus, depending on the state of progress, the surgeon can be informed of the zone in which he or she is to operate and/or of zones in which there is no need to intervene or of a zone in which special care must be taken (for example, a zone which has an artery passing through it).

The zone may also correspond to the processing elements that have been taken into account to determine the state of progress; the surgeon or any person involved in the operative procedure or any operator of the computer system can thus verify that the state of progress calculation has taken the relevant elements into account. This verification may be followed by a validation step. Thus, if the surgeon or the third-party operator confirms that the elements taken into account are relevant then the process can continue; conversely, if it is confirmed that the elements taken into account are not relevant then the surgeon can be informed that the reliability of the state of progress determination is low. The determination of whether the elements taken into account are relevant, i.e., identifying whether the determined group of processing elements is relevant to determining the state of progress, can be carried out automatically (for example, by comparing to an operative protocol) or manually with the knowledge of the surgeon.

According to one embodiment, the information dependent on the state of progress includes images from the reference sequence of images, starting with the image corresponding to the state of progress.

The surgeon can thus see the progress of a similar operative procedure. Moreover, the part of the sequence of images which is displayed on the display means corresponds to the same operative step as the one for which the state of progress has been determined, i.e. the step currently in progress.

According to another aspect, a computer program is proposed comprising instructions which, when executed by a processor, implement a method for processing a video stream related to a specific operative procedure comprising:

receiving, via the video stream reception interface, the video stream comprising a sequence of images including an image to be processed which represents at least a portion of an anatomical element, said image to be processed being formed by processing elements;

determining, by means of a processing function, whether or not a criterion is satisfied in the image to be processed, the processing function being composed of a first parameterized function and a second parameterized function:

parameters of the first parameterized function being obtained by a machine learning algorithm on the basis of an image from a reference sequence of images such that the result of the first parameterized function applied to the image allows determining the processing elements of the image which represent the portion of the anatomical element, the reference sequence of images being previously recorded and related to the specific operating procedure, the image from the reference sequence of images representing at least a portion of an anatomical element, parameters of the second parameterized function being obtained by a machine learning algorithm on the basis of the image from the reference sequence of images that is combined with a result of the first parameterized function applied to the image from the reference sequence of images such that the result of the second parameterized function applied to the image combined with a result of the first parameterized function applied to the image allows determining whether or not the criterion is satisfied;

determining a state of progress associated with the image to be processed, based on whether or not the criterion is satisfied, the state of progress being representative of a state of progress of an operative step of the specific operative procedure.

According to another aspect of the subject disclosure, a non-transitory, computer-readable storage medium is provided on which such a program is stored.

According to another aspect of the subject disclosure, a system is proposed comprising the video stream processing device, a camera comprising an endoscope connected to the video stream reception interface.

BRIEF DESCRIPTION OF THE DRAWINGS

Other features, details, and advantages of the subject disclosure will become apparent upon reading the detailed description below, and upon analyzing the appended drawings, in which.

DETAILED DESCRIPTION

Figure 1:
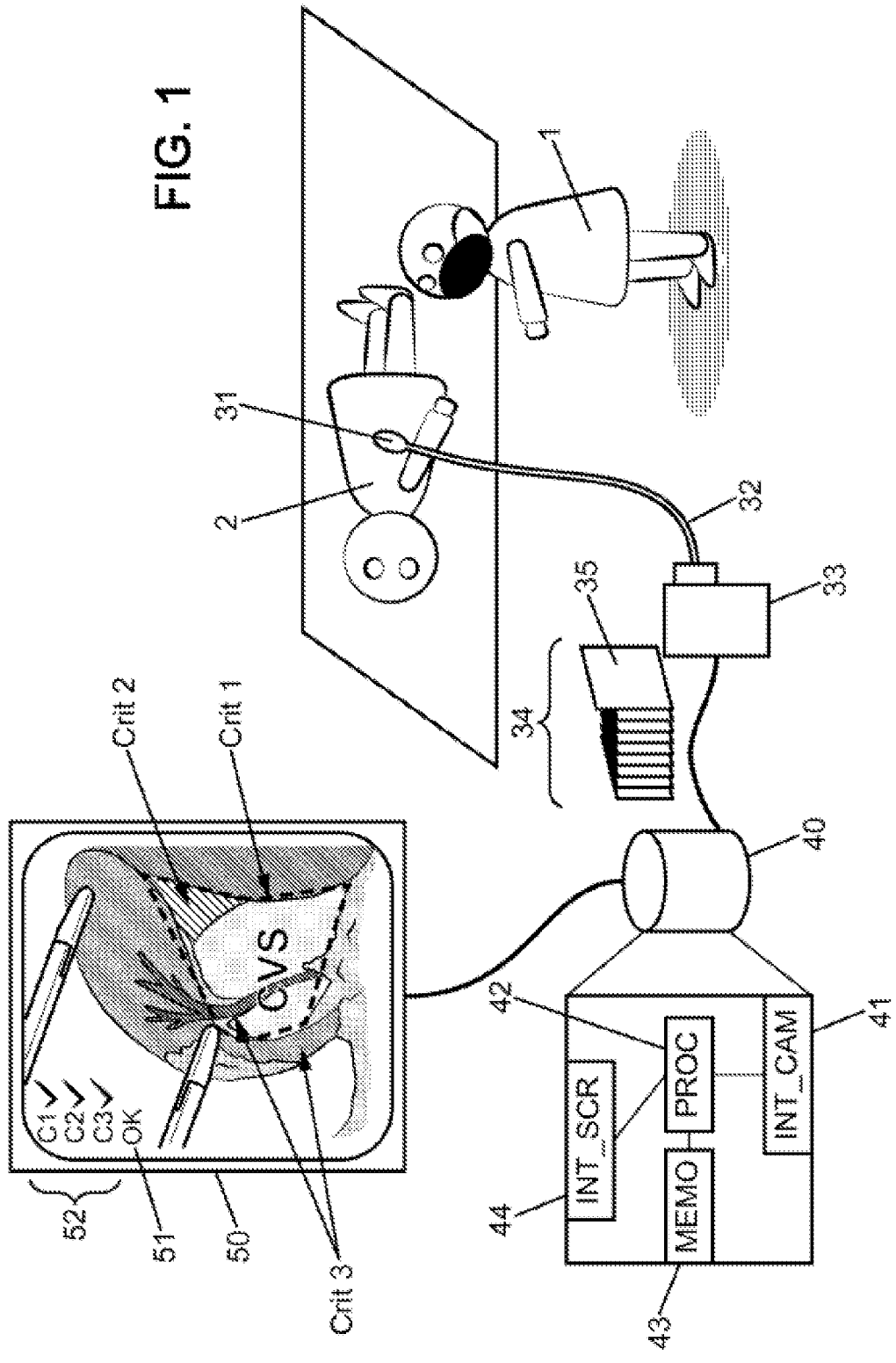
FIG. 1 illustrates the device according to a particular embodiment.

The example in FIG. 1 describes an operating room where a surgeon 1 is performing a specific operative procedure, for example a cholecystectomy (removal of the gallbladder) on a patient 2.

The operative procedure takes place with a surgical camera comprising a lens 31, an optical fiber 32, and an encoding module 33 which makes it possible to convert the light signal coming from the lens 31 and transferred by the optical fiber 32 into a digital signal, namely a video stream. The surgical camera shown here is a laparoscopic camera. Any other surgical camera device may be employed with the subject disclosure.

The video stream comprises a sequence of images 34 encoded in a video format, for example an MPEG format. This video stream is transmitted to the video stream processing device 40.

The video stream processing device 40 comprises an interface module interfacing with the surgical camera (INT_CAM) 41, a processor (PROC) 42, a memory (MEMO) 43, and an interface module interfacing with a display means (INT_SCR) 44.

The processor 42 is configured to determine, by means of the processing function F, whether or not the processed images satisfy the criteria (Crit 1, Crit 2, Crit 3) and to determine the states of progress associated with the processed images 35.

The processor 42 may be configured to determine the parameters of the first and second parameterized functions by means of reference sequences of images which have been recorded prior to the operative procedure underway, and may be stored in the video stream processing device 40 or in a remote database (not shown on FIG. 1).

The processor 42 is configured to store the images of the sequence which are critical.

The processor 42 is configured to determine a level of risk related to an anatomical element exhibiting an abnormality.

The processor 42 is configured to determine deviations between an operative protocol and situations in the operative procedure which correspond to the images 35.

The processor 42 is also configured to control the interface module interfacing with the surgical camera (INT_CAM) 41 in order to be able to receive the video stream coming from the encoding module 33 of the surgical camera.

The processor 42 is also configured to control the interface module interfacing with the display means (INT_SCR) 44 in order to be able to display to the surgeon 1 the video stream accompanied by various information.

The memory 43 comprises a non-volatile memory in which the computer program is stored and a volatile memory in which the parameters of the parameterized functions are stored (namely the parameters of the function $f_1$ (first parameterized function) which carries out the segmentation of the images to be processed 35 and of the criteria test function $f_2$ (second parameterized function)), the images of the video stream, the information to be displayed on the display means, etc.

Once the sequence of images 34 has been processed, the video stream processing device 40 can transmit information to be displayed on a display means 50, via the interface module interfacing with the display means (INT_SCR) 44.

The display means 50 of FIG. 1 is a screen in the operating room, but any other display means used in the context of surgical operations may be used, for example augmented reality glasses.

The video stream processing device 40 and the display means may not be located in the operating room or even in the buildings where the operating room is located. For example, the video stream processing device 40 may be in a data center which hosts services related to information technology (IT), and the display means may be in the room where the surgeon 1 is located, a room which may not be the operating room where the patient 2 is located in the case of a remote surgical operation.

Critical images in the sequence may be stored in a hospital database or in an external data center.

Figure 2:
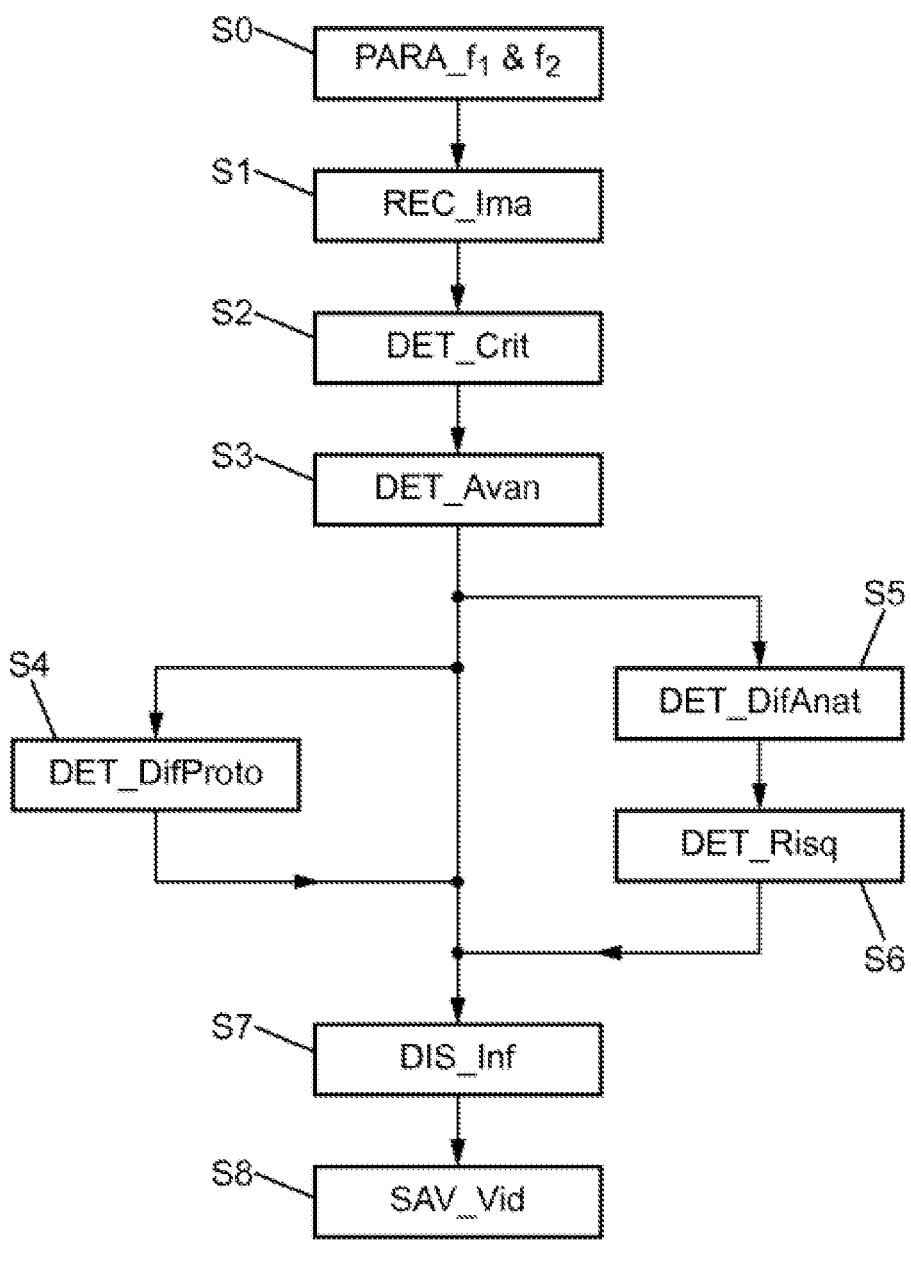
FIG. 2 illustrates a flowchart representing an implementation of the device according to a particular embodiment.

FIG. 2 shows a flowchart of a method according to one particular embodiment.

In step S0, the device is configured for a certain type of operative procedure, for example a cholecystectomy or ablation of the gallbladder in the case described here. For this purpose, a processing function F is determined and stored in the memory 43 of device 40.

The processing function F is composed of two functions, a first parameterized function $f_1$ and a second parameterized function $f_2$. The first parameterized function $f_1$ allows segmentation of the images 35 to be processed, the second parameterized function $f_2$ allows testing whether the criteria C1, C2, and C3 are satisfied in the image I. The function F may for example associate, with an image I to be processed, the triplet (c1, c2, c3) obtained by $F(I)=f_2(I, f_1(I))$. The couple (I, $f_1$(I)) may be an n-tuple (M1, . . . , Mn) of matrices whose cells represent the processing elements. The values of the cells of matrix M1 represent the red color level in the RGB color code, each cell of matrix M1 representing a processing element (for example a pixel) of the image I to be processed 35. The values of the cells of matrix M2 represent the green color level in the RGB color code, each cell of matrix M2 representing a processing element (for example a pixel) of the image I to be processed 35. The values of the cells of matrix M3 represent the blue color level in the RGB color code, each cell of matrix M3 representing a processing element (for example a pixel) of the image I to be processed 35. Each of the matrices M4 to Mn corresponds to a different anatomical element. Each cell of matrix Mi (for i ranging from 4 to n) represents a processing element (for example a pixel) of the image I to be processed 35, the value (for example 0 or 1) of the cell coding whether or not the processing element represents a portion of the anatomical element corresponding to matrix Mi. $f_1$(I) corresponds to matrices M4 to Mn, for example $f_1$(I)=(M4, . . . , Mn). The image I to be processed 35 is represented by matrices M1, M2, and M3. Other representations of the couple (I, $f_1$(I)) are possible and do not affect the application of the subject disclosure. For example, M1, M2, and M3 may be replaced by a single matrix whose cells directly represent the RGB code. Thus, $f_1$ associates matrices (M4, . . . , Mn) with the image I to be processed 35. For example, if the segmentation of the image is carried out on the basis of seven anatomical elements, then $f_1$ associates matrices (M4, . . . , M10) with the image I to be processed 35. Each of the matrices corresponds to an anatomical element, for example the gallbladder (M4), the cystic duct (M5), the cystic artery (M6), the hepatocystic triangle (M7), and the liver bed (M8), to which are added the surgical tools (M9) and the background (M10). For a pixel of the image I to be processed 35, the cells of the matrices corresponding to this pixel will respectively indicate 1 as the value if the pixel represents a portion of these anatomical elements (or the tools and the background) and 0 if the pixel does not represent a portion of these anatomical elements (or the tools and the background).

The function $f_2$ respectively associates, with the couple (I, $f_1$(I)), the triplet (c1, c2, c3) representing whether or not each predefined criterion (Crit 1, Crit 2, Crit 3) is validated. Thus:

c1 can take the value of "1" when the hepatocystic triangle (more precisely the processing elements representing the hepatocystic triangle in the image) does not include fatty and fibrous tissues (more precisely, processing elements representing fatty and fibrous tissues) (Crit 1), and "0" otherwise;

c2 can take the value of "1" when the lower third of the gallbladder is separated from the liver to expose the liver bed (Crit 2), and "0" otherwise;

c3 can take the value of "1" when it is apparent that the cystic duct and the cystic artery are entering the gallbladder (Crit 3), and "0" otherwise.

The parameters of the two parameterized functions $f_1$ and $f_2$ are determined, in particular by using machine learning algorithms, then stored in memory 43.

The first parameterized function $f_1$ may be defined as an artificial neural network of one or more layers of neurons. Each neuron of a layer of the network is an activation function whose inputs are weighted values from outputs of the previous layer. The activation functions may be, for example, sigmoid functions, hyperbolic tangent functions, or Heaviside step functions. The weights constitute the parameters of function $f_1$. To determine these parameters, a machine learning algorithm is used with images from reference videos (or from reference sequences of images). The machine learning algorithm thus determines the parameters in order to minimize the distance between the results of $f_1$ when $f_1$ is applied to the images and the expected results, namely the expected values of the cells of matrices M4 to M10. The expected values may be determined by a specialist in the field related to the specific operative procedure, for example by determining the various anatomical elements in each image used (to determine the parameters).

Similarly to the first parameterized function $f_1$, the second parameterized function $f_2$ may be defined as an artificial neural network of one or more layers of neurons. Each neuron of a layer of the network is an activation function whose inputs are weighted values from outputs of the previous layer. The activation functions may be, for example, sigmoid functions, hyperbolic tangent functions, or Heaviside step functions. The weights constitute the parameters of function $f_2$. To determine these parameters, a machine learning algorithm is used with images from reference videos (or from reference sequences of images). The machine learning algorithm thus determines the parameters in order to minimize the distance between the results of function $f_2$ when $f_2$ is applied to the reference combinations and the expected results, namely the values c1, c2, and c3 indicated above. The distance is thus minimized between the expected values c1, c2 and c3 and the results of function $f_2$ when $f_2$ is applied to n-tuples of the matrices (M1, . . . , M10) corresponding to images from the reference sequences of images used to carry out the learning.

Once the parameters of the parameterized functions $f_1$ and $f_2$ have been identified by means of a database containing reference videos related to the specific operative procedure, namely a cholecystectomy in this case, these are stored in memory 43.

In step S1, the video stream processing device 40 receives data, via the interface module interfacing with the surgical camera 41, corresponding to the encoding of the last image 35 of the sequence of images 34 (or video stream). For example, the video stream processing device 40 receives data in an MPEG format corresponding to the last image 35. The images in the sequence of images 34 that were previously received are being processed or have already been processed by the video stream processing device 40. The last image 35 is therefore the next image to be processed. If the video stream is not interrupted, other images will be received by the device 40 and will be processed after image 35.

In step S2, the processor 42 applies the processing function F to the image 35 in order to obtain the triplet of values (c1, c2, c3) related to the three criteria considered (Crit 1, Crit 2, Crit 3). The image 35 may be represented by a triplet of matrices (M1, M2, M3) as indicated above. Thus, the result of F on this matrix triplet can be obtained by $F(M1, M2, M3)=f_2[(M1, M2, M3), f_1(M1, M2, M3)]=f_2(M1, . . . , M10)$.

The processing function F is advantageously applied in a single step to the triplet of matrices representing the processed image 35 (M1, M2, M3), even if the processing of the image 35 can also be carried out in two steps, namely the application of the first parameterized function $f_1$ to the triplet of matrices (M1, M2, M3) then the application of the second parameterized function $f_2$ to the combination of the image 35 (i.e. the triplet of matrices (M1, M2, M3)) and the result of the first parameterized function $f_1$ (i.e. the 7-tuple of matrices (M4, . . . , M10)), i.e. the application of the second parameterized function $f_2$ to the n-tuplet (M1, . . . , M10). In cases where the processing function is applied in two steps, an optional verification may be applied to the results of the first parameterized function $f_1$ in order to easily validate or monitor the relevance of the results of the processing function F.

Thus, in the example of FIG. 1, the result of the processing function F is (c1, c2, c3)=(1, 1, 1), i.e. the three criteria are satisfied. The result of the processing function F may be a triplet of values, each value indicating a level of confidence that the criterion has been satisfied. For example, if (c1, c2, c3)=(58, 32, 99) then we consider this as 58% confidence that criterion 1 is satisfied, 32% confidence that criterion 2 is satisfied, and 99% confidence that criterion 3 is satisfied.

In step S3, the processor 42 determines a state of progress of the operative step associated with the last image 35, on the basis of the criteria that are satisfied or not satisfied for this image. In the example of FIG. 1, the operative step of the specific operative procedure is a preparatory step required before definitive ablation of the gallbladder. The three predefined criteria (Crit 1, Crit 2, Crit 3) having been satisfied, the state of progress of the preparatory step is "final" (or 100% of the preparatory step has been completed) in the image 35 from the sequence of images 34. The preparatory step can thus be considered as complete. If one of the criteria is not met, then the state of progress of the preparatory step is incomplete (or 66% of the preparatory step has been completed). If two criteria are not met, then the state of progress of the preparatory step is incomplete (or 33% of the preparatory step has been completed). Or, if none of the criteria are met, then the state of progress of the preparatory step is "initial" (or 0% of the preparatory step has been completed).

The state of progress is associated with an image (here image 35) in the sequence of images 34. Thus, the processor 42 may have calculated a state of progress for each image in the sequence of images 34.

In step S4, the processor 42 determines a deviation from an operative protocol, on the basis of the state of progress calculated in step S4.

The deviation may be an indicator requiring the processing of several images from the sequence of images 34. Indeed, while the state of progress may be a state at a time t of the capture of the image 35, the deviation may be an analysis considering the sequence of the states of progress (i.e. the sequence in validating the criteria). The processor 42 can thus calculate the evolution in the states of progress of the sequence of images 34 and deduce a deviation from this, for example:

a difference in the validation order for the predefined criteria compared to the validation order for the criteria up to the same state of progress of the protocol; or/and a difference between the portion of the anatomical element the surgeon is acting on and the one which, in view of the protocol, should be concerned by the surgeon's actions immediately after the state of progress calculated in step S3;

a difference between the evolution of the state of progress of the sequence of images 34.

This step is optional.

In step S5, the processor 42 determines deviations between characteristic values of a group of processing elements, i.e. a set of processing elements representing a portion of an anatomical element, and reference characteristic values (for example, averages of the characteristics of groups of processing elements which represent the same portion of the anatomical element) related to the same state of progress as the state of progress associated with the image 35. For determining the deviations, ranges of values may be determined. The deviations thus correspond to the fact that groups of pixels have characteristics (size, shape, arrangement, or color) whose values lie outside the ranges of values containing the reference values, i.e. portions of anatomical elements for which the characteristics are abnormal.

In step S6, the processor 42 determines the levels of risk related to each deviation determined in step S5. Several levels of risk may be provided for each characteristic, which then correspond to several ranges of values nested one inside the other. The level of risk is related to risks associated with the operative procedure performed.

Steps S5 and S6 are part of an embodiment which may be combined with the other embodiments, for example the one described in step S4. However, these steps are optional.

In step S7, the processor 42 controls the interface module 44 interfacing with the display means, in order to display information on the display means 50. The information to be displayed is information dependent on the state of progress determined in step S3. The display means in the example of FIG. 1 is a screen located in the operating room, and the information displayed on it is intended for the surgeon performing the operative procedure. However, the display means may be of any other type (glasses, projector, etc.) and may be intended for someone other than the surgeon, for example, an administrative member of the clinic or hospital or even a surgeon supervising the operative procedure.

The information displayed may be:

information dependent on the deviation from an operative protocol determined in step S4 (which may be presented in the form of an alert). Thus, the screen may show that the criteria have not been validated in the order required by the protocol. The screen may also display that the anatomical element on which the surgeon is acting does not correspond to an anatomical element which, at that stage in the state of progress, is involved in the protocol context. It may also display information indicating that the state of progress does not correspond to that of the operative protocol, for example a state of progress changing very quickly at the start of the operative step concerned then very slowly;

information indicating that one of the criteria tested in step S2 is not satisfied;

information indicating the criteria satisfied as described in FIG. 1 where some information 52 indicates that the three criteria have been satisfied (i.e. validated);

information validating a step of an operative step or information authorizing the start of a next operative step. In the example of FIG. 1, after the three criteria are satisfied, the preparatory step is validated by an "OK" 51;

information about the level of risk determined in step S6;

a zone indicated in the image 35. This zone may indicate the zone where a surgical action is to be performed. Conversely, this zone may indicate a zone where no surgical action is to be performed or where there is an anatomical element at risk;

information on the state of progress of the operative step, determined in step S3;

images from a reference sequence of images (or a reference video) related to the specific operative procedure, the images or the video being images corresponding to a state of progress identical to or subsequent to the one determined in step S3.

The information may be displayed in combination with the image 35, as is the case in the example of FIG. 1. This information may be adapted to the criticality of the operative step currently in progress and the criticality of the information to be displayed. Thus, the criteria validation confirmation may be displayed in a more discreet manner than the information concerning the level of risk or even the zone in which an anatomical element at risk is located. The information displayed on the screen of FIG. 1 is displayed at the top left of the screen; any other layout is possible.

Steps S2 to S7 can be repeated as long as the encoding module 33 is sending images to be processed.

In step S8, the processor 42 controls the device to store (or store with greater definition and/or while retaining more images of this portion of the video stream compared to the storage of the rest of the video stream) images of the sequence temporally comprised around an image from the sequence of images (for example, the images in the next minute of video following image 35), according to the criticality of the operative step related to the state of progress.

The critical or non-critical nature of an operative step may be indicated by the operative protocol.

The storage may be performed in memory 43 or in a data center. It is thus possible to retain a greater amount of video streams by giving priority to retaining the relevant parts of these streams.

The invention claimed is:

1. A device for processing a video stream related to a specific operative procedure, said device comprising:
   a video stream reception interface,
   a processor, and
   a memory storing instructions, such that when these instructions are executed by the processor, they configure the device for:
   receiving, via the video stream reception interface, the video stream comprising a sequence of images including an image to be processed which represents at least a portion of an anatomical element, said image to be processed being formed by processing elements;
   determining, by means of a processing function, whether or not a criterion is satisfied in the image to be processed, the processing function being composed of a first parameterized function and a second parameterized function:
   parameters of the first parameterized function being obtained by a machine learning algorithm on the basis of an image from a reference sequence of images such that the result of the first parameterized function applied to the image allows determining the processing elements of the image which represent the portion of the anatomical element, the reference sequence of images being previously recorded and related to the specific operative procedure, the image from the reference sequence of images representing at least a portion of an anatomical element, and
   parameters of the second parameterized function being obtained by a machine learning algorithm on the basis of the image from the reference sequence of images combined with a result of the first parameterized function applied to the image from the reference sequence of images such that the result of the second parameterized function applied to the image, combined with a result of the first parameterized function applied to the image, allows determining whether or not the criterion is satisfied; and determining a state of progress associated with the image to be processed, based on whether or not the criterion is satisfied, the state of progress being representative of a state of progress of an operative step of the specific operating procedure.

2. The device according to claim 1, wherein, when the instructions are executed by the processor, they configure the device for:

based on the determined state of progress, storing images from the sequence of images that are within a time interval around the image to be processed.

3. The device according to claim 2, wherein the number of images stored is dependent on the criticality of the operative step and/or on the determined state of progress.

4. The device according to claim 1, further comprising a display means and wherein, when the instructions are executed by the processor, they configure the device for displaying on the display means, with the image to be processed, information dependent on the state of progress.

5. The device according to claim 4, wherein, when the instructions are executed by the processor, they configure the device for:

determining a deviation from an operative protocol, on the basis of the state of progress;

where the information dependent on the state of progress is dependent on the determined deviation.

6. The device according to claim 4, wherein the display of information dependent on the state of progress is according to a criticality of the operative step represented by the state of progress.

7. The device according to claim 4, wherein the information dependent on the state of progress comprises information indicating that the criterion is not validated.

8. The device according to claim 4, wherein the information dependent on the state of progress comprises information validating a step of an operative step or information authorizing the start of a next operative step.

9. The device according to claim 4, wherein, when the instructions are executed by the processor, they configure the device for:

determining a deviation between at least one value of a characteristic of a group of processing elements of the image which represent the portion of the anatomical element and a reference value, the reference value being an average of the value of the characteristic of groups of processing elements which represent the portion of the anatomical element and related to the same state of progress as the state of progress;

determining a level of risk associated with this deviation;

wherein the information dependent on the state of progress includes the level of risk.

10. The device according to claim 4, wherein the information dependent on the state of progress includes:

a zone in which a surgical action is to be performed; and/or a zone in which there is no surgical action; and/or a zone in which there is an anatomical element requiring special attention; and/or a zone corresponding to processing elements that are considered in order to determine the state of progress.

11. The device according to claim 4, wherein the information dependent on the state of progress includes images from the reference sequence of images, starting with the image corresponding to the state of progress.

12. A non-transitory computer-readable medium encoded with executable instructions which, when executed, causes an apparatus comprising a processor operatively coupled with a memory, to perform a method for processing a video stream related to a specific operative procedure, the method comprising:

receiving, via the video stream reception interface, the video stream comprising a sequence of images including an image to be processed which represents at least a portion of an anatomical element, said image to be processed being formed by processing elements;

determining, by means of a processing function, whether or not a criterion is satisfied in the image to be processed, the processing function being composed of a first parameterized function and a second parameterized function:

parameters of the first parameterized function being obtained by a machine learning algorithm on the basis of an image from a reference sequence of images such that the result of the first parameterized function applied to the image allows determining the processing elements of the image which represent the portion of the anatomical element, the reference sequence of images being previously recorded and related to the specific operative procedure, the image from the reference sequence of images representing at least a portion of an anatomical element, parameters of the second parameterized function being obtained by a machine learning algorithm on the basis of the image from the reference sequence of images that is combined with a result of the first parameterized function applied to the image from the reference sequence of images such that the result of the second parameterized function applied to the image combined with a result of the first parameterized function applied to the image allows determining whether or not the criterion is satisfied;

determining a state of progress associated with the image to be processed, based on whether or not the criterion is satisfied, the state of progress being representative of a state of progress of an operative step of the specific operative procedure.

13. The non-transitory computer-readable medium according to claim 12, wherein, when the instructions are executed by the processor, they configure the device for:

based on the determined state of progress, storing images from the sequence of images that are within a time interval around the image to be processed.

14. The non-transitory computer-readable medium according to claim 12, wherein the number of images stored is dependent on the criticality of the operative step and/or on the determined state of progress.

15. The non-transitory computer-readable medium according to claim 12, further comprising a display means and wherein, when the instructions are executed by the processor, they configure the device for:

displaying on the display means, with the image to be processed, information dependent on the state of progress.

16. The non-transitory computer-readable medium according to claim 15 wherein, when the instructions are executed by the processor, they configure the device for:

determining a deviation from an operative protocol, on the basis of the state of progress;

where the information dependent on the state of progress is dependent on the determined deviation.

17. The non-transitory computer-readable medium according to claim 15, wherein the display of information dependent on the state of progress is according to a criticality of the operative step represented by the state of progress.

18. The non-transitory computer-readable medium according to claim 15, wherein the information dependent on the state of progress comprises information indicating that the criterion is not validated.

19. The non-transitory computer-readable medium according to claim 15, wherein the information dependent on the state of progress comprises information validating a step of an operative step or information authorizing the start of a next operative step.

20. The non-transitory computer-readable medium according to claim 15 wherein, when the instructions are executed by the processor, they configure the device for:

determining a deviation between at least one value of a characteristic of a group of processing elements of the image which represent the portion of the anatomical element and a reference value, the reference value being an average of the value of the characteristic of groups of processing elements which represent the portion of the anatomical element and related to the same state of progress as the state of progress;

determining a level of risk associated with this deviation; wherein the information dependent on the state of progress includes the level of risk.

* * * * *